United States Patent
Kaleta et al.

(10) Patent No.: US 10,456,249 B2
(45) Date of Patent: Oct. 29, 2019

(54) PROSTHETIC HEART VALVE WITH PARAVALVULAR LEAK MITIGATION FEATURES

(71) Applicant: St. Jude Medical, Cardiology Division, Inc., St. Paul, MN (US)

(72) Inventors: Richard Kaleta, Arden Hills, MN (US); Keith High, White Bear Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1 day.

(21) Appl. No.: 15/702,941

(22) Filed: Sep. 13, 2017

(65) Prior Publication Data

US 2018/0071089 A1 Mar. 15, 2018

Related U.S. Application Data

(60) Provisional application No. 62/394,837, filed on Sep. 15, 2016.

(51) Int. Cl.
*A61F 2/24* (2006.01)
*A61F 2/915* (2013.01)

(52) U.S. Cl.
CPC .......... *A61F 2/2418* (2013.01); *A61F 2/2421* (2013.01); *A61F 2/915* (2013.01);
(Continued)

(58) Field of Classification Search
CPC ...... A61F 2/2418; A61F 2/2421; A61F 2/915; A61F 2210/0014; A61F 2220/0025;
(Continued)

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 B4 | 5/2005 |
| DE | 10121210 B4 | 11/2005 |

(Continued)

OTHER PUBLICATIONS

International Search Report for Application No. PCT/US2017/051258, dated Dec. 11, 2017.

(Continued)

*Primary Examiner* — Brian E Pellegrino
*Assistant Examiner* — Rebecca Lynee Zimmerman
(74) *Attorney, Agent, or Firm* — Lerner, David, Littenberg, Krumholz & Mentlik, LLP

(57) ABSTRACT

A prosthetic heart valve includes a collapsible and expandable stent with a valve assembly disposed therein. A first cuff is positioned on the lumenal or ablumenal surface of the stent. A second cuff is positioned radially outward of the stent and the first cuff. The second cuff may include apertures that allow blood to pass through the second cuff into the spaces between the first and second cuffs. The second cuff may include a proximal edge with a plurality of notches that may be closed to create puckered areas in the second cuff to facilitate the movement of blood in the spaces between the first and second cuffs. The stent may include struts adjacent the second cuff that bow radially inwardly to create additional space for blood to flow in the spaces between the first and second cuffs.

4 Claims, 8 Drawing Sheets

(52) U.S. Cl.
CPC .............. *A61F 2210/0014* (2013.01); *A61F 2220/0025* (2013.01); *A61F 2250/0063* (2013.01); *A61F 2250/0069* (2013.01)

(58) Field of Classification Search
CPC ...... A61F 2250/0063; A61F 2250/0069; A61F 2002/077
See application file for complete search history.

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,591,197 A * | 1/1997 | Orth | A61F 2/07 606/191 |
| 5,843,167 A | 12/1998 | Dwyer et al. | |
| 5,855,601 A | 1/1999 | Bessler et al. | |
| 5,857,216 A * | 1/1999 | Gold | A41D 19/02 2/169 |
| 5,935,163 A | 8/1999 | Gabbay | |
| 5,961,549 A | 10/1999 | Nguyen et al. | |
| 6,045,576 A | 4/2000 | Starr | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,652,578 B2 | 11/2003 | Bailey et al. | |
| 6,685,625 B2 | 2/2004 | Gabbay | |
| 6,716,244 B2 | 4/2004 | Klaco | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,951,573 B1 | 10/2005 | Dilling | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,195,641 B2 | 3/2007 | Palmaz et al. | |
| 7,247,167 B2 | 7/2007 | Gabbay | |
| 7,267,686 B2 | 9/2007 | DiMatteo et al. | |
| 7,276,078 B2 | 10/2007 | Spenser et al. | |
| 7,311,730 B2 | 12/2007 | Gabbay | |
| 7,320,704 B2 | 1/2008 | Lashinski et al. | |
| 7,329,278 B2 | 2/2008 | Seguin et al. | |
| 7,374,573 B2 | 5/2008 | Gabbay | |
| 7,381,218 B2 | 6/2008 | Schreck | |
| 7,381,219 B2 | 6/2008 | Salahieh et al. | |
| 7,452,371 B2 | 11/2008 | Pavcnik et al. | |
| 7,510,572 B2 | 3/2009 | Gabbay | |
| 7,510,575 B2 | 3/2009 | Spenser et al. | |
| 7,524,331 B2 | 4/2009 | Birdsall | |
| 7,534,261 B2 | 5/2009 | Friedman | |
| RE40,816 E | 6/2009 | Taylor et al. | |
| 7,585,321 B2 | 9/2009 | Cribier | |
| 7,628,805 B2 | 12/2009 | Spenser et al. | |
| 7,682,390 B2 | 3/2010 | Seguin | |
| 7,708,775 B2 | 5/2010 | Rowe et al. | |
| 7,731,742 B2 | 6/2010 | Schlick et al. | |
| 7,748,389 B2 | 7/2010 | Salahieh et al. | |
| 7,780,725 B2 | 8/2010 | Haug et al. | |
| 7,799,069 B2 | 9/2010 | Bailey et al. | |
| 7,803,185 B2 | 9/2010 | Gabbay | |
| 7,824,442 B2 | 11/2010 | Salahieh et al. | |
| 7,837,727 B2 | 11/2010 | Goetz et al. | |
| 7,846,203 B2 | 12/2010 | Cribier | |
| 7,846,204 B2 | 12/2010 | Letac et al. | |
| 7,892,281 B2 | 2/2011 | Seguin et al. | |
| 7,914,569 B2 | 3/2011 | Nguyen et al. | |
| 7,959,666 B2 | 6/2011 | Salahieh et al. | |
| 7,959,672 B2 | 6/2011 | Salahieh et al. | |
| 7,972,378 B2 | 7/2011 | Tabor et al. | |
| 7,988,724 B2 | 8/2011 | Salahieh et al. | |
| 7,993,394 B2 | 8/2011 | Hariton et al. | |
| 8,016,877 B2 | 9/2011 | Seguin et al. | |
| D648,854 S | 11/2011 | Braido | |
| 8,048,153 B2 | 11/2011 | Salahieh et al. | |
| 8,052,741 B2 | 11/2011 | Bruszewski et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,075,611 B2 | 12/2011 | Millwee et al. | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| 8,137,398 B2 | 3/2012 | Tuval et al. | |
| 8,142,497 B2 | 3/2012 | Friedman | |
| D660,432 S | 5/2012 | Braido | |
| D660,433 S | 5/2012 | Braido et al. | |
| D660,967 S | 5/2012 | Braido et al. | |
| 8,182,528 B2 | 5/2012 | Salahieh et al. | |
| 8,221,493 B2 | 7/2012 | Boyle et al. | |
| 8,230,717 B2 | 7/2012 | Matonick | |
| 8,231,670 B2 | 7/2012 | Salahieh et al. | |
| 8,252,051 B2 | 8/2012 | Chau et al. | |
| 8,308,798 B2 | 11/2012 | Pintor et al. | |
| 8,313,525 B2 | 11/2012 | Tuval et al. | |
| 8,323,335 B2 | 12/2012 | Rowe et al. | |
| 8,323,336 B2 | 12/2012 | Hill et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,348,998 B2 | 1/2013 | Pintor et al. | |
| 8,366,769 B2 | 2/2013 | Huynh et al. | |
| 8,403,983 B2 | 3/2013 | Quadri et al. | |
| 8,408,214 B2 | 4/2013 | Spenser | |
| 8,414,643 B2 | 4/2013 | Tuval et al. | |
| 8,425,593 B2 | 4/2013 | Braido et al. | |
| 8,449,599 B2 | 5/2013 | Chau et al. | |
| 8,449,604 B2 | 5/2013 | Moaddeb et al. | |
| 8,454,686 B2 | 6/2013 | Alkhatib | |
| 8,500,798 B2 | 8/2013 | Rowe et al. | |
| 8,568,474 B2 | 10/2013 | Yeung et al. | |
| 8,579,962 B2 | 11/2013 | Salahieh et al. | |
| 8,579,966 B2 | 11/2013 | Seguin et al. | |
| 8,585,755 B2 | 11/2013 | Chau et al. | |
| 8,591,575 B2 | 11/2013 | Cribier | |
| 8,597,349 B2 | 12/2013 | Alkhatib | |
| 8,603,159 B2 | 12/2013 | Seguin et al. | |
| 8,603,160 B2 | 12/2013 | Salahieh et al. | |
| 8,613,765 B2 | 12/2013 | Bonhoeffer et al. | |
| 8,623,074 B2 | 1/2014 | Ryan | |
| 8,652,204 B2 | 2/2014 | Quill et al. | |
| 8,663,322 B2 | 3/2014 | Keranen | |
| 8,668,733 B2 | 3/2014 | Haug et al. | |
| 8,685,080 B2 | 4/2014 | White | |
| 8,728,154 B2 | 5/2014 | Alkhatib | |

(56) References Cited

U.S. PATENT DOCUMENTS

| | | | |
|---|---|---|---|
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1* | 11/2006 | Nguyen ............... A61F 2/2412 623/2.18 |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0234443 A1 | 9/2009 | Ottma et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2013/0282113 A1* | 10/2013 | Punga ............... A61F 2/2418 623/2.17 |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277423 A1 | 9/2014 | Alkhatib et al. |
| 2014/0303719 A1 | 10/2014 | Cox et al. |
| 2014/0324164 A1 | 10/2014 | Gross et al. |
| 2014/0330371 A1* | 11/2014 | Gloss ............... A61F 2/2418 623/2.17 |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2017/0014229 A1* | 1/2017 | Nguyen-Thien-Nhon ............... A61F 2/2418 |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| FR | 2847800 B1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |
| WO | 2001049213 A2 | 7/2001 |
| WO | 0154625 A1 | 8/2001 |
| WO | 2001056500 A2 | 8/2001 |
| WO | 200176510 A2 | 10/2001 |
| WO | 0236048 A1 | 5/2002 |

(56) References Cited

FOREIGN PATENT DOCUMENTS

| | | |
|---|---|---|
| WO | 0247575 A2 | 6/2002 |
| WO | 2002067782 A2 | 9/2002 |
| WO | 2003047468 A1 | 6/2003 |
| WO | 2005070343 A1 | 8/2005 |
| WO | 06073626 A2 | 7/2006 |
| WO | 2007053243 A2 | 5/2007 |
| WO | 2007071436 A2 | 6/2007 |
| WO | 08070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2015126711 A1 | 8/2015 |
| WO | 2017011697 A1 | 1/2017 |

OTHER PUBLICATIONS

Andersen, H. R., et al., "Transluminal implantation of artificial heart valves", European Heart Journal, (1992), vol. 13, Issue 5, 704-708.
Andersen, Henning Rud, "Transluminal Catheter Implanted Prosthetic Heart Valves", International Journal of Angiology 7:102-106, 1998.
Buellesfeld et al., "Treatment of paravalvular leaks through inverventional techniques", Department of Cardiology, Ben University Hospital 2011.
Christoph H. Huber, et al., "Direct-Access Valve Replacement", Journal of the American College of Cardiology, vol. 16, No. 2, (Jul. 19, 2005).
De Cicco, Giuseppe, et al., "Aortic valve periprosthetic leakage: anatomic observations and surgical results", The Annals of thoracic surgery 79.5 (2005): 1480-1485.
Dewey et al., "Transapical aortic valve implantation: an animal feasibility study"; The annals of thoracic surgery 2006; 82: 110-6 (Feb. 13, 2006).
Gössl et al., "Percutaneous treatment of aortic and mitral valve paravalvular regurgitation", Current cardiology reports 15.8, 2013: 1-8.
Heat Advisor, "Heart repairs without surgery. Minimally invasive procedures aim to correct valve leakage", Sep. 2004, PubMed ID 15586429.
Hourihan et al., "Transcatheter Umbrella Closure of Valvular and Paravalvular Leaks", Journal of the American College of Cardiology, vol. 20, No. 6, pp. 1371-1377, (1992).
John G. Webb et al., "Percutaneous Aortic Valve Implantation Retrograde From the Femoral Artery", Circulation, 2006; 113:842-850 (Feb. 6, 2006).
M. J. Mack, "Minimally invasive cardiac surgery", Surgical Endoscopy, 2006, 20:S488-S492, DOI: 10.1007/s00464-006-0110-8 (presented Apr. 24, 2006).
Moazami, Nader, et al., "Transluminal Aortic Valve Placement", ASAIO Journal, (1996); 42:M381-M385.
Muñoz et al., "Guidance of treatment of perivalvular prosthetic leaks", Current cardiology reports 16.1, Jan. 2014: 1-6.
Duaden, Rene et al., "Percutaneous aortic valve replacement: resection before implantation", 836-840, European J. of Cardio-thoracic Surgery, 27 (2005).
Rohde et al., "Resection of Calcified Aortic Heart Leaflets in Vitro by Q-Switched 2pm Microsecond Laser Radiation", Journal of Cardiac Surgery, 30: 157-162, 2015, dol: 10.1111/jocs.12481.
Ruiz, Carlos, "Overview of PRE-CE Mark Transcatheter Aortic Valve Technologies", Euro PCR, dated May 25, 2010.
Samuel V. Lichtenstein et al., "Transapical Transcatheter Aortic Valve Implantation in Humans", Circulation. 2006; 114: 591-596 (Jul. 31, 2006).
Samuel V. Lichtenstein, "Closed heart surgery: Back to the future", The Journal of Thoracic and Cardiovascular Surgery, 2006, vol. 131, No. 5, pp. 941-943.
Swiatkiewicz, Iwona, et al., "Percutaneous closure of mitral perivalvular leak", Kardiologia polska 67.7 (2009): 762.
Textbook "Transcatheter Valve Repair", 2006, pp. 165-186.
Walther et al., "Transapical approach for sutureless stent-fixed aortic valve implantation: experimental results", European Journal of Cardio-thoracic Surgery 29 (2006) 703-708 (Jan. 30, 2006).
Zegdi, Rachid, MD, PhD et al., "Is It Reasonable to Treat All Calcified Stenotic Aortic Valves With a Valved Stent?", 579-584, J. of the American College of Cardiology, vol. 51, No 5, Feb. 5, 2008.
Knudsen, L.L., et al., "Catheter-implanted prosthetic heart valves", The International Journal of Artificial Organs, vol. 16, No. 5 1993, pp. 253-262.

\* cited by examiner

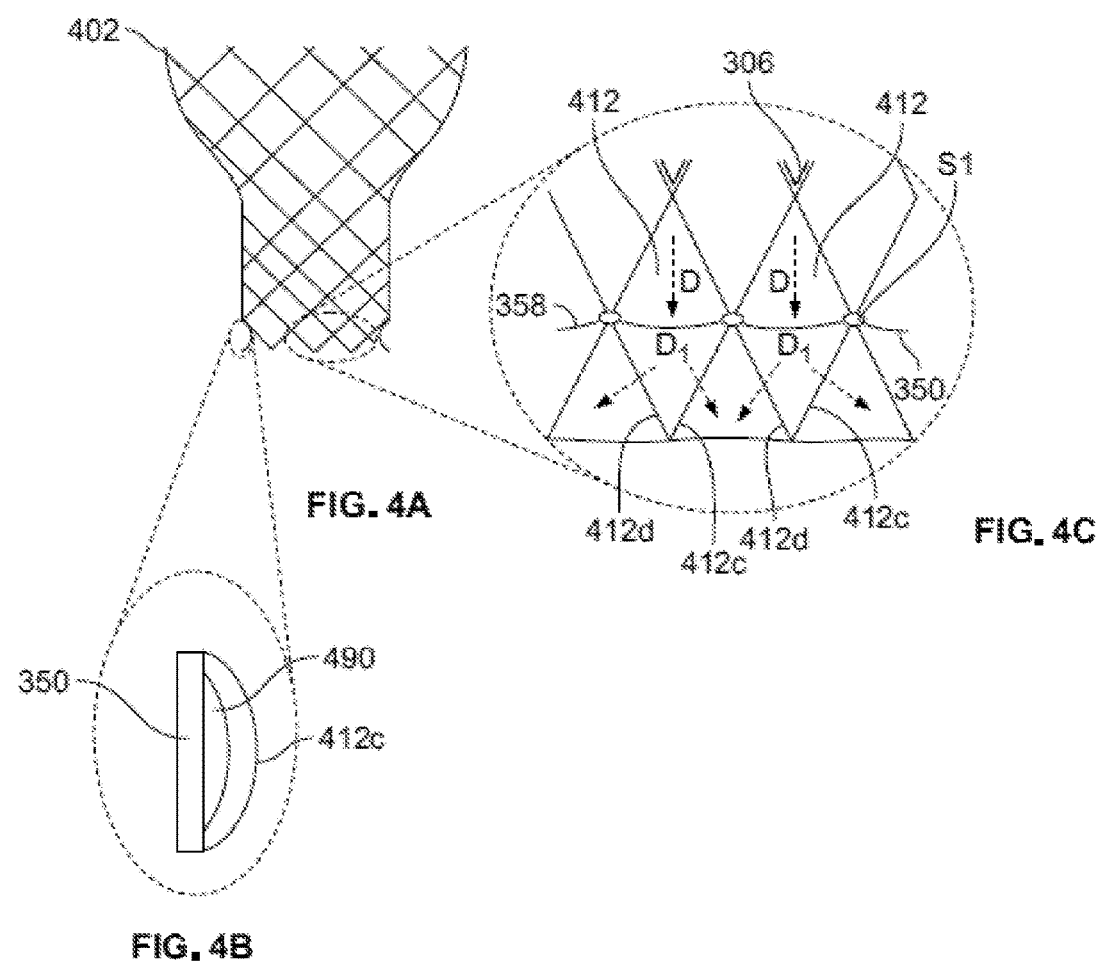

PROSTHETIC HEART VALVE WITH PARAVALVULAR LEAK MITIGATION FEATURES

CROSS-REFERENCE TO RELATED APPLICATIONS

This application claims the benefit of the filing date of U.S. Provisional Patent Application No. 62/394,837 filed Sep. 15, 2016, the disclosure of which is hereby incorporated by reference herein.

BACKGROUND OF THE DISCLOSURE

The present disclosure relates to heart valve replacement and, in particular, to collapsible prosthetic heart valves. More particularly, the present disclosure relates to collapsible prosthetic transcatheter heart valves which minimize or reduce paravalvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

After implantation, imperfect sealing between the cuff and the site of implantation may cause complications such as paravalvular leakage ("PV leak"), or blood flowing through one or more gaps formed between the structure of the implanted valve and cardiac tissue.

BRIEF SUMMARY

According to one aspect of the disclosure, a prosthetic heart valve for replacing a native valve includes a stent extending in an axial direction between an inflow end and an outflow end and having circumferential rows of cells formed by cell struts, the stent having a collapsed condition and an expanded condition. A valve assembly is disposed within the stent. A first cuff is disposed on a lumenal surface of the stent. A second cuff has a proximal edge facing toward the inflow end of the stent and a distal edge facing toward the outflow end of the stent, the second cuff being annularly disposed about one of the circumferential rows of cells and positioned radially outward of the first cuff and the stent. An ablumenal surface of selected cell struts forming the one circumferential row of cells has a concave curvature in a length direction of the selected cell struts of the stent when the stent is in the expanded condition.

According to another aspect of the disclosure, a prosthetic heart valve for replacing a native valve includes a stent extending in an axial direction between an inflow end and an outflow end, the stent having a collapsed condition and an expanded condition. A valve assembly is disposed within the stent. A first cuff is disposed on a lumenal surface of the stent. A second cuff has a proximal edge facing toward the inflow end of the stent and a distal edge facing toward the outflow end of the stent. The second cuff is annularly disposed about the stent and positioned radially outward of the first cuff and the stent. The second cuff includes a plurality of notches at spaced apart locations along the proximal edge, each of the notches defining a void in the proximal edge of the second cuff. The second cuff has an initial configuration in which the voids render the proximal edge of the second cuff discontinuous, and a gathered configuration in which the voids are closed so that the proximal edge of the second cuff is substantially continuous. The proximal edge of the second cuff in the gathered configuration has a length that is less than the length of the proximal edge of the second cuff in the initial configuration. The second cuff is coupled to at least one of the stent and the first cuff so that in the expanded condition of the stent, the second cuff is in the gathered configuration.

According to a further aspect of the disclosure, a stent extending in an axial direction from an inflow end to an outflow end has a collapsed condition and an expanded condition. A valve assembly is disposed within the stent. A first cuff is annularly disposed on a lumenal or ablumenal surface of the stent. A second cuff has a proximal edge facing toward the inflow end of the stent and a distal edge facing toward the outflow end of the stent, the second cuff being annularly disposed about the stent and positioned radially outward of the first cuff and the stent. The second cuff includes a plurality of apertures.

BRIEF DESCRIPTION OF THE DRAWINGS

Various embodiments of the presently disclosed prosthetic heart valve may be more fully understood with reference to the following detailed description when read with the accompanying drawings, in which:

FIG. 4A is a highly schematic longitudinal cross-sectional view of a stent according to another embodiment of the disclosure;

FIG. 4B is a side view of a portion of an outer cuff on the stent of FIG. 4A in an expanded condition;

FIG. 4C is a highly schematic view of retrograde blood flowing into a portion of the outer cuff on the stent of FIG. 4A;

DETAILED DESCRIPTION

As used herein, the term "inflow end," when used in connection with a prosthetic heart valve, refers to the end of the heart valve through which blood enters when the valve is functioning as intended. As used herein, the term "proximal" refers to the inflow end of a prosthetic heart valve or to elements of a prosthetic heart valve that are relatively close to the inflow end, and the term "distal" refers to the outflow end of a prosthetic heart valve or to elements of a prosthetic heart valve that are relatively close to the outflow end. The term "outflow end," when used in connection with a prosthetic heart valve, refers to the end of the heart valve through which blood exits when the valve is functioning as intended. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the "lengthwise direction" or "axial direction" refer to a direction along a longitudinal axis passing through the center of the stent or heart valve. When used herein in the context of a prosthetic heart valve, or a component thereof, the "circumferential direction" refers to a direction extending along the circumference of the prosthetic heart valve in a direction orthogonal to the longitudinal axis.

Figure 1:
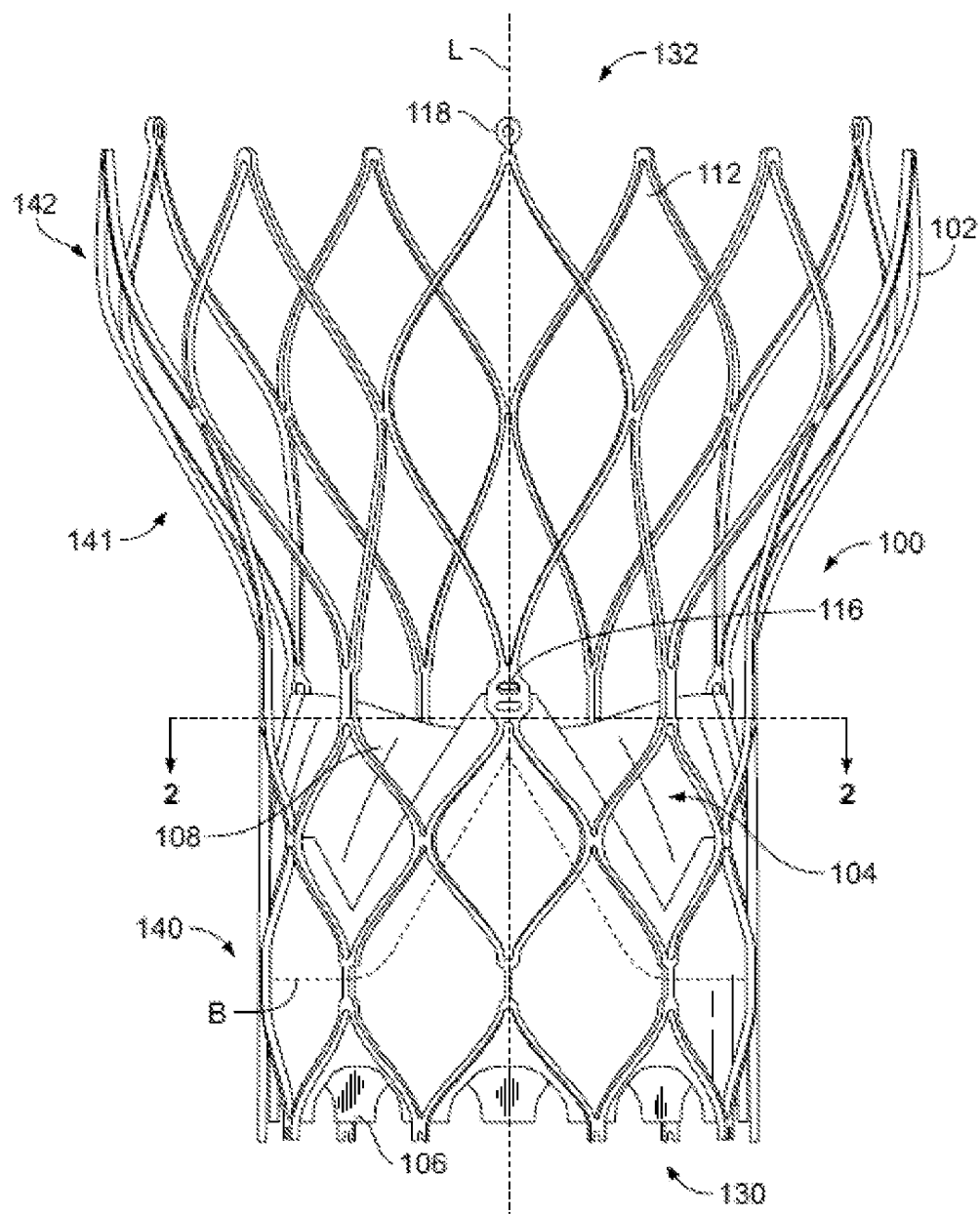
FIG. 1 is a front view of a collapsible prosthetic heart valve according to the prior art.

FIG. 1 shows a collapsible stent-supported prosthetic heart valve 100 in an expanded condition according to the prior art. The prosthetic heart valve 100 is designed to replace the function of a native aortic valve of a patient. The prosthetic heart valve 100 includes a stent constructed as a frame 102. The stent 102 extends from an inflow or annulus end 130 to an outflow or aortic end 132 along a lengthwise or longitudinal axis L, and includes an annulus section 104 adjacent the inflow end 130 and an aortic section 142 adjacent the outflow end 132. The annulus section 104 has a relatively small cross-section in the expanded condition, while the aortic section 142 has a relatively large cross-section in the expanded condition. The annulus section 104 may be in the form of a cylinder having a substantially constant diameter along its length. A transition section 141 may taper outwardly from the annulus section 104 to the aortic section 142. Each of the sections of the stent 102 includes a plurality of cells 112 connected to one another in one or more annular rows around the stent 102. For example, as shown in FIG. 1, the annulus section 104 may have two annular rows of complete cells 112 and the aortic section 142 and the transition section 141 may each have one or more annular rows of complete or partial cells 112. The cells 112 in the aortic section 142 may be larger than the cells 112 in the annulus section 104. The larger cells 112 in the aortic section 142 may better enable the prosthetic valve 100 to be positioned without the structure of the stent 102 interfering with blood flow to the coronary arteries. At least partly due to the shape of cells 112, the stent 102 elongates in the direction of axis L as cells 112 collapse when the stent 102 is transitioned from the expanded condition to the collapsed condition.

The stent 102 may include one or more retaining elements 118 at the outflow end 132, the retaining elements 118 being sized and shaped to cooperate with retaining structures provided on a deployment device (not shown). The engagement of the retaining elements 118 with the retaining structures on the deployment device may help maintain the prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is shown in U.S. Patent Publication No. 2012/0078352, the entire contents of which are hereby incorporated by reference herein.

The stent 102 may also include a plurality of commissure attachment features or points 116 for mounting the commissures of the valve assembly to the stent 102. As can be seen in FIG. 1, each commissure attachment feature 116 may lay at the intersection of four cells 112, two of the cells 112 being adjacent one another in the same annular row, and the other two cells 112 being in different annular rows and lying in end to end relationship. The commissure attachment features 116 may be positioned entirely within the annulus section 104 or at the juncture of annulus section 104 and transition section 141, and may include one or more eyelets which facilitate the suturing of the leaflet commissures to the stent. The stent 102 may be formed as a unitary structure, for example, by laser cutting or etching a tube of a super elastic and/or shape memory metal alloy such as a nickel-titanium alloy of the type sold under the designation nitinol. Such a unitary structure can also be referred to as a "non-woven" structure, in that it is not formed by weaving or winding one or more filaments.

The prosthetic heart valve 100 includes a valve assembly 140 positioned at least partially in the annulus section 104. The valve assembly includes a cuff 106 and a plurality of leaflets 108 that collectively function as a one way valve by coapting with one another. As FIG. 1 illustrates a prosthetic heart valve for replacing a native aortic valve, the prosthetic heart valve is shown with three leaflets 108. Two leaflets join one another at each of three commissures. When implanted at the native aortic valve annulus, blood flows from the inflow end 130, past leaflets 108, and toward the outflow end 132. This occurs when the pressure in the left ventricle is greater than the pressure in the aorta, forcing the leaflets 108 to open. When the pressure in the aorta is greater than the pressure in the left ventricle, the leaflets 108 are forced closed and coapt with one another along free edges of the leaflets 108, blocking blood from flowing through the prosthetic heart valve in a retrograde fashion from the outflow end 132 to the inflow end 130. The valve assembly 140 may be mounted to the stent 102 by suturing the commissures of the leaflets 108 to each of the three commissure attachment features 116 and suturing other portions of the leaflets 108 to the stent 102 and/or cuff 106, or by other methods known in the art. It will be appreciated that the prosthetic heart valves according to aspects of the disclosure may have a greater or lesser number of leaflets 108 and commissure attachment features 116 than shown in FIG. 1 and described above. Each leaflet 108 may define a leaflet belly B, indicated with broken lines in FIG. 1. The leaflet belly B is the portion of valve assembly 140 above which leaflets 108 are free to move radially inwardly to coapt with one another along their free edges.

Although the cuff 106 is shown in FIG. 1 as being disposed on the lumenal or inner surface of the annulus section 104, the cuff 106 may be disposed on the ablumenal or outer surface of annulus section 104, or may cover all or part of either or both of the lumenal and ablumenal surfaces of the annulus section 104. As is shown in FIG. 1, in one example the entirety of the valve assembly 140, including the leaflet commissures, is positioned in the annulus section 104 of the stent 102. When open, the leaflets may extend further into the transition section 141 or may be designed such that they remain substantially completely within the annulus section 104. In this embodiment, substantially the entirety of the valve assembly 140 is positioned between the inflow end 130 of stent 102 and the commissure attachment features 116, and none of the valve assembly is positioned between the commissure attachment features 116 and the outflow end 132 of the stent 102.

In operation, the embodiment of the prosthetic heart valve 100 described above may be used to replace a native heart valve, such as the aortic valve, a surgical heart valve, or a heart valve that has undergone a surgical procedure. The prosthetic heart valve 100 may be delivered to the desired site (e.g., near a native aortic annulus) using any suitable delivery device. During delivery, the prosthetic heart valve 100 is disposed inside the delivery device in the collapsed condition. The delivery device may be introduced into a patient using any known procedures, such as a transfemoral, transapical, subclavian or transseptal approach. Once the delivery device has reached the target site, the user may deploy the prosthetic heart valve 100. Upon deployment, the prosthetic heart valve 100 expands into secure engagement within the native aortic annulus. When the prosthetic heart valve 100 is properly positioned inside the heart, it works as a one-way valve, allowing blood to flow in one direction and preventing blood from flowing in the opposite direction.

Figure 2:
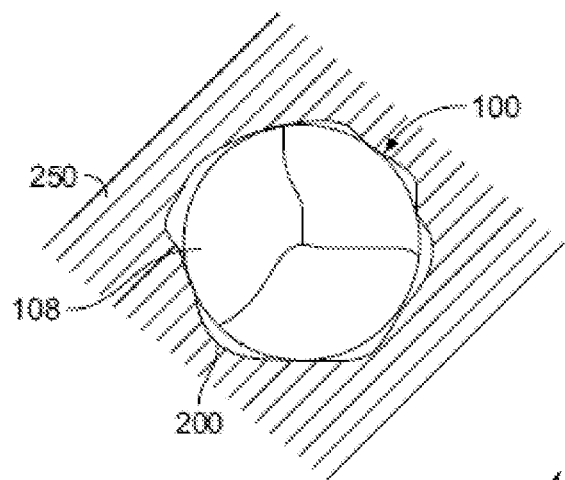
FIG. 2 is a highly schematic transverse cross-sectional view of the prior art prosthetic heart valve implanted in a patient, taken along line 2-2 of FIG. 1.

FIG. 2 is a highly schematic transverse cross-sectional illustration of the prosthetic heart valve 100 having leaflets 108 disposed within the native valve annulus 250, taken along line 2-2 shown in FIG. 1. As seen in FIG. 2, the substantially circular annulus section 104 of the stent 102 is disposed within a non-circular native valve annulus 250. At certain locations around the perimeter of the prosthetic heart valve 100, gaps 200 form between the heart valve 100 and the native valve annulus 250. Blood flowing through these gaps and around the outside of the valve assembly 140 of the prosthetic heart valve 100 can result in PV leak or regurgitation and other inefficiencies which can reduce cardiac performance. Such improper fitment may be due to suboptimal native valve annulus geometry due, for example, to calcification of the native valve annulus 250 or due to unresected native leaflets.

Figure 3A:
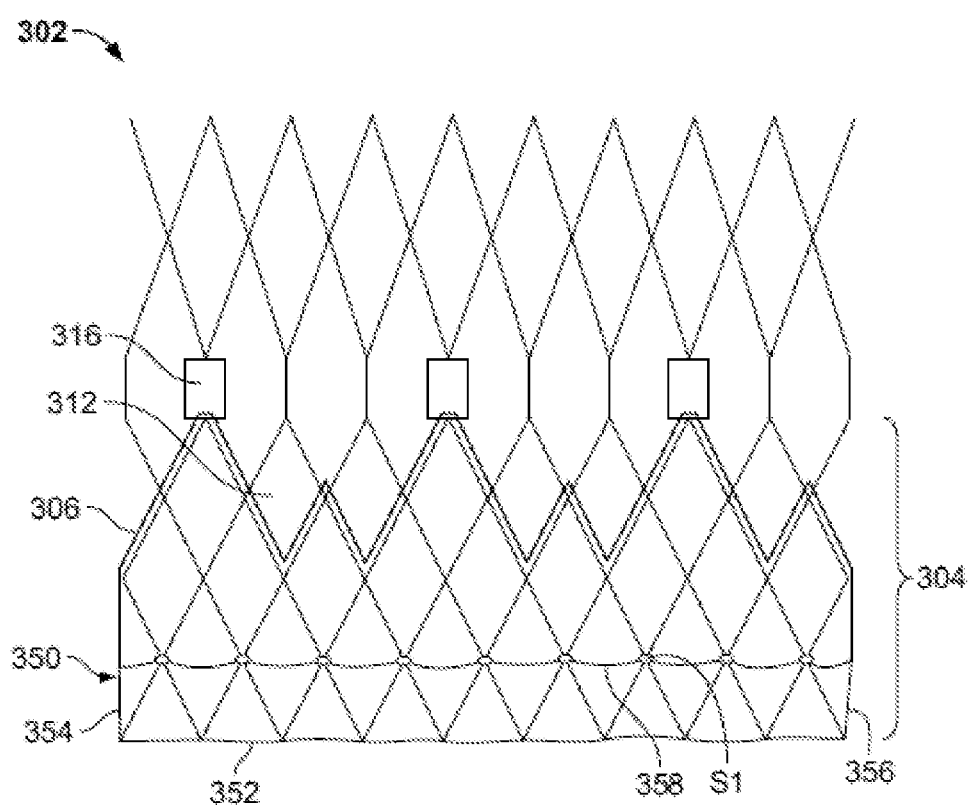
FIG. 3A is a schematic view of a stent according to an embodiment of the disclosure in a flattened condition with an inner cuff and an outer cuff.

FIG. 3A illustrates a stent 302 of a prosthetic heart valve according to an aspect of the disclosure. Stent 302 may be used in a prosthetic heart valve that is similar or identical to prosthetic heart valve 100 described above with certain exceptions. For example, annulus section 304 of stent 302 may include three rows of cells 312 instead of two rows, although stent 302 may alternatively include two rows of cells 312 in annulus section 304. It should be understood that, while commissure attachment features 316 of stent 302 are illustrated as open rectangles, the commissure attachment features 316 may take a form similar to commissure attachment features 116, or any other suitable form including any number of rows or columns of eyelets and/or eyelets of different sizes and/or shapes positioned in any arrangement on the commissure attachment feature. A cuff 306 similar or identical to cuff 106 may be positioned on the lumenal and/or ablumenal surface of stent 302. Although cuff 106 is shown as scalloped at its inflow end, cuff 306 may have a straight inflow end rather than a scalloped one. In order to help eliminate PV leak, for example through the gaps 200 shown in FIG. 2, additional material may be coupled to the exterior of stent 302 as an outer cuff 350. In the illustrated example, outer cuff 350 may have a substantially rectangular shape and may be wrapped around the circumference of stent 302 at its inflow end. Outer cuff 350 may be positioned anywhere along the height of stent 302, so long as the proximal edge of the outer cuff is either at the proximal edge of inner cuff 306 or between the proximal and distal edges of the inner cuff, and the distal edge of the outer cuff is either at the distal edge of the inner cuff or between the proximal and distal edges of the inner cuff. With this positioning, outer cuff 350 is positioned on stent 302 so as to overlap in the longitudinal direction of stent 302 with inner cuff 306. Outer cuff 350 may be a single piece of material including a proximal edge 352, two side edges 354, 356, and a distal edge 358. Preferably, the proximal edge 352 of outer cuff 350 is coupled to the stent 302 and/or to the inner cuff 306 along a proximal edge of the stent 302 and/or a proximal edge of the inner cuff 306, for example by a continuous line of sutures (not shown), so that retrograde blood flow entering the space between the outer cuff 350 and the inner cuff 306 cannot pass in the retrograde direction beyond the combination of cuffs. In order to allow retrograde blood flow to enter the space between the outer cuff 350 and the inner cuff 306, the distal edge 358 may be attached at spaced apart locations to the stent 302 and/or the inner cuff 306. In the illustrated example, the distal edge 358 of outer cuff 350 is sutured to stent 302 at attachment points S1 which are located at the intersection of each cell 312 in the proximalmost row of cells with an adjacent cell 312 in that same row. In the illustrated example, since there are nine cells 312 in the proximalmost row, there are nine separate points of attachment S1 where the distal edge 358 is coupled to stent 302 and/or inner cuff 306. Retrograde blood flow around the ablumenal surface of stent 302 may enter the pocket or space between outer cuff 350 and inner cuff 306 via the space between any two adjacent attachment points S1. Once retrograde blood flow enters this space, the outer cuff 350 may tend to billow outwardly, helping to seal any of the gaps 200 between the prosthetic heart valve and the native annulus 250. It should be understood that although the term "inner" is used in connection with cuff 306, that is merely intended to indicate that cuff 306 is positioned radially inward of outer cuff 350. However, inner cuff 306 may be located either on the lumenal or ablumenal surface of stent 302, or on both surfaces. It should be understood that in FIG. 3A, only part of the outline of inner cuff 306 is visible, as a bottom or proximal end of inner cuff 306 is positioned behind outer cuff 350 in the view of FIG. 3A.

Although described as a single piece of material above, outer cuff 350 may comprise multiple pieces of material that in the aggregate form a similar shape and provide similar function to that described above for outer cuff 350. Also, rather than being formed as a structure that is wrapped around the circumference of stent 302, outer cuff 350 may be formed as a continuous tube without defining distinct side edges 354, 356. Preferably, outer cuff 350 has an axial height measured from proximal edge 352 to distal edge 358 that is approximately half the axial height of the cells 312 in the proximalmost row of stent 302 as measured along the major axes of the cells between two apices when the cells are in an expanded condition. However, other heights of outer cuff 350 may be suitable, such as the full axial height of the cells 312 in the proximalmost row of cells, or more or less than the full axial height of such cells 312. However, different heights of outer cuff 350 may result in a change of the position of attachment points S1. For example, if outer cuff 350 is formed with a height equal to the full axial height of the cells 312 in the proximalmost row of cells, the attachment points S1 could be positioned at the distalmost apex of such cells 312. Still further, although the outer cuff 350 is described above as separate from the inner cuff 306, the outer cuff 350 may be integral with the inner cuff 306, the combined cuff wrapping around the inflow end of stent 302. With this configuration, the proximal edge 352 of outer cuff 350 does not need to be sutured to stent 302, although it still may be preferable to provide such attachment. Both the inner cuff 306 and the outer cuff 350 may be formed of the same or different materials, including any suitable biological material or polymer such as, for example, polytetrafluoroethylene (PTFE), ultra-high molecular weight polyethylene (UHMWPE), polyurethane, polyvinyl alcohol, polyester, silicone, or combinations thereof.

Figure 3B:
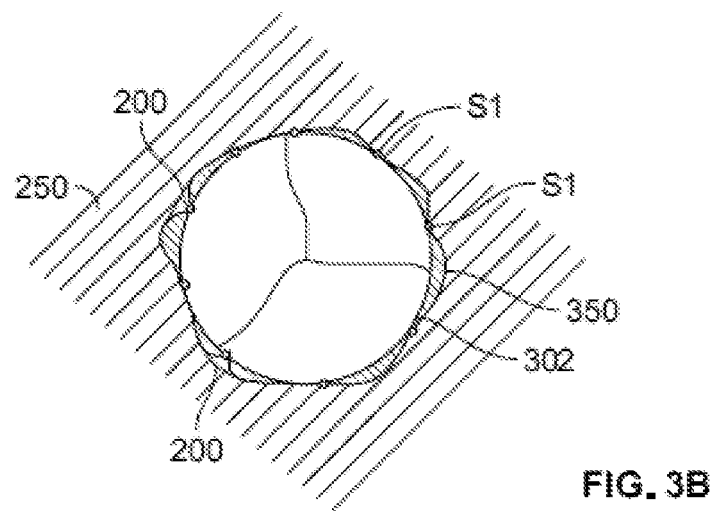
FIG. 3B is a highly schematic transverse cross-sectional view of a prosthetic heart valve including the stent and outer cuff of FIG. 3A implanted in a patient.
Figure 3C:
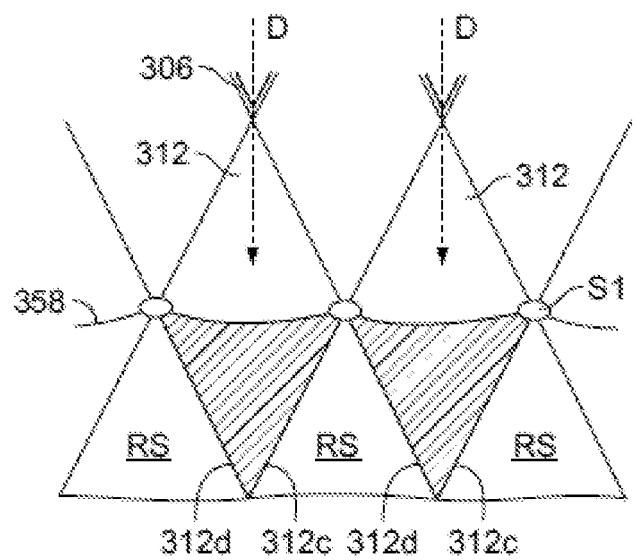
FIG. 3C is a highly schematic view of retrograde blood flowing into a portion of the outer cuff on the stent of FIG. 3A.
Figure 3D:
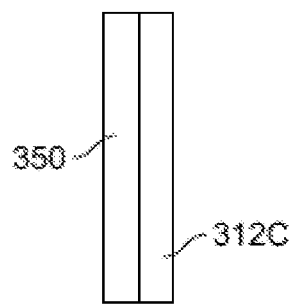
FIG. 3D is a side view of a portion of the outer cuff on the stent of FIG. 3A in an expanded condition.

As shown in FIG. 3B, when a prosthetic heart valve including stent 302 and outer cuff 350 is implanted into a native valve annulus 250, retrograde blood flow may cause outer cuff 350 to billow radially outward and fill gaps 200. However, after retrograde blood flow passes the distal edge 358 of outer cuff 350 and enters the space between the outer cuff and the inner cuff 306, that blood may not easily be able to migrate past the cell struts located between the inner and outer cuffs toward the proximal edges of the cuffs when certain conditions are present. This point is illustrated in FIG. 3C. As blood flows in the retrograde direction D around the ablumenal surface of stent 302, the blood can enter the space between outer cuff 350 and inner cuff 306 via the openings between attachment points S1, as described above. If a condition exists in which outer cuff 350 is taut when stent 302 is in the expanded condition, blood may not be able to pass across struts 312c and 312d into the space of adjacent cells (or half-cells), such as those directly under attachment points S1. As shown in FIG. 3D, if outer cuff 350 is taut when stent 302 is in the expanded condition, there may be little or no open space between outer cuff 350 and struts 312c, as well as between outer cuff 350 and struts 312d. Even when subjected to the pressure causing retrograde blood to flow into the space between outer cuff 350 and inner cuff 306, little or none of that blood may migrate past cell struts 312c and 312d into the restricted spaces RS. By providing additional and/or alternative structures as described in greater detail below, the outer cuff 350 may be provided with an enhanced ability to billow outwardly to fill gaps 200.

FIG. 4A shows a longitudinal cross-sectional view of a stent 402 that may be identical to stent 302, with certain exceptions described below. Stent 402 may be used with an inner cuff and outer cuff similar or identical to inner cuff 306 and outer cuff 350, respectively. In particular, stent 402 may include two rows of cells 412 in an annulus section, with inner cuff 306 and outer cuff 350 coupled to stent 402 in a similar or identical manner to that described in connection with stent 302. However, whereas the annulus section 304 of stent 302 may be substantially cylindrical when in the expanded condition, certain struts of stent 402 may be bowed radially inwardly. For example, struts 412c and/or struts 412d of cells 412 in the proximalmost row of cells of stent 402 may be bowed, arched, or otherwise curved radially inwardly so that, when stent 402 is in the expanded condition, a center portion of each of these curved struts 412c, 412d is positioned radially inwardly of proximal and distal portions of those curved struts. The curvature of struts 412c and/or struts 412d may be such that the terminal ends of these curved struts are positioned a substantially equal distance in the radial direction from the longitudinal axis of stent 402, and the center portions of these struts are positioned at a lesser distance in the radial direction from the longitudinal axis. The lumenal surface of struts 412c and 412d may have a convex curvature along the entire length of the struts between their proximal and distal ends, with the ablumenal surface of those struts having a concave curvature along the entire length of the struts between their proximal and distal ends. With this configuration, as best seen in FIG. 4B, when outer cuff 350 is taut and stent 402 is in the expanded condition, there is an open space 490 between struts 412c and outer cuff 350, as well as between struts 412d and outer cuff 350, due to the curvature of those struts. As shown in FIG. 4C, retrograde blood may enter the space between outer cuff 350 and inner cuff 306 by flowing in the retrograde direction D between adjacent points of attachment S1 of the distal edge 358 of outer cuff 350 to the stent 402 and/or internal cuff 306. The blood between outer cuff 350 and inner cuff 306 may readily flow across struts 412c and 412d in the directions $D_1$ by way of the open space 490 between outer cuff 350 and the center portions of struts 412c and 412d, so that any portion of outer cuff 350 adjacent a gap 200 may be able to billow outwardly to fill that gap. Although it is preferable that each strut 412c and 412d in the proximalmost row of cells is curved as described above, providing a similar curvature to some but less than all of these struts, such as only struts 412c and not struts 412d, or only struts 412d and not struts 412c, may provide a similar benefit. Struts 412c and 412d may be set to the desired shape in a similar or identical fashion as the remainder of the stent 402 is shape-set, for example by heat-setting.

Figures 4D, 5A:
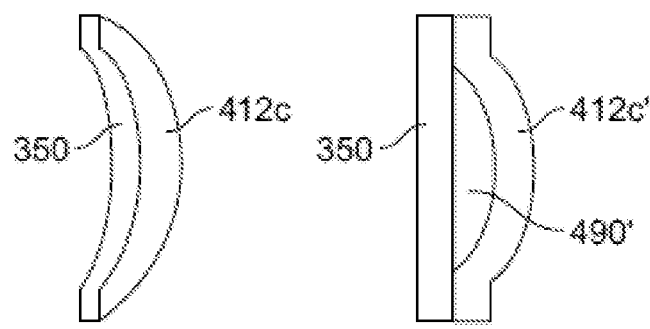
FIG. 4D is a side view of a portion of an outer cuff on the stent of FIG. 4A in a collapsed condition.
FIG. 5A is a side view of a portion of an outer cuff on an alternate embodiment of a stent in an expanded condition.

The shape of struts 412c and 412d may be set so that the curvature described above completely or substantially remains when stent 402 is the collapsed condition. This feature may result in a reduction in the forces encountered upon loading the prosthetic valve into a delivery device in the collapsed condition. For example, as shown in FIG. 4D, portions of outer cuff 350 adjacent the curved portions of struts 412c and 412d may nest or otherwise sit along the curved struts 412c and 412d, which may reduce the overall bulkiness of the prosthetic heart valve in those areas. However, it should be understood that in this and other embodiments described herein, the struts 412c and/or 412d may take other shapes upon stent 402 collapsing. For example, struts 412c and 412d may become substantially parallel to a longitudinal axis of the stent when in the collapsed condition in some embodiments.

Figure 5B:
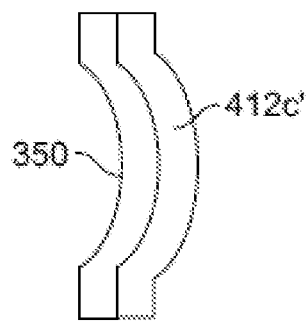
FIG. 5B is a side view of a portion of the outer cuff on the stent of FIG. 5A in a collapsed condition.

FIGS. 4A-D illustrate an embodiment of stent 402 in which the struts 412c and 412d in the cells 412 in the proximalmost row of cells are curved or bowed radially inwardly along substantially the entire length of those struts. However, alternative shapes also may be suitable. For example, FIGS. 5A-B illustrate a strut 412c' of a stent and the outer cuff 350 of a prosthetic heart valve that is identical in every way to the prosthetic heart valve including stent 402 and outer cuff 350 described above, except for the curvature of the struts corresponding to struts 412c and 412d. In particular, although struts 412c' are bowed radially inwardly so that a center portion of each strut is positioned radially inwardly of proximal and distal portions of that strut when the stent is in the expanded condition, the struts 412c' are not curved along substantially their entire length. Rather, proximal and distal portions of struts 412c' may be positioned substantially within the same cylindrical surface of revolution about the longitudinal axis of the stent, which surface also includes the struts in other cells in the annulus section of the stent. In other words, the portion of struts 412c' that is bowed radially inward may be isolated to a center portion of the struts, with the proximal and distal portions lacking such curvature. Thus, the lumenal surface of the center portion of strut 412c' may have a convex curvature in the length direction of that strut, while the ablumenal surface of the center portion of the strut has a convex curvature in the same length direction. The proximal and distal end portions of strut 412c', however, may each be substantially straight in the length direction of the strut, and may be collinear. In this embodiment, the bowed portion of each strut 412c' and the outer cuff 350 together define an open space 490', generally similar to open space 490, that may allow for blood positioned between outer cuff 350 and inner cuff 306 to migrate across struts 412c', even if outer cuff 350 is taut. Although not illustrated in FIGS. 5A-B, it should be understood that struts corresponding to struts 412d may have the same or similar shape and curvature as struts 412c'. Also, similar to the embodiment described in connection with FIGS. 4A-D, the curvature of struts 412c' (and the similarly shaped struts corresponding to struts 412d) may result in a reduction in the forces encountered upon loading the prosthetic valve into a delivery device in the collapsed condition, where portions of outer cuff 350 nest or otherwise sit along the curved portions of the struts. Other benefits that may be provided by the embodiment shown in FIGS. 5A-B may include easier fabrication, the facilitation of proper resheathing of the valve during surgery if desired, and maintaining consistent outward radial force of the stent on the native anatomy.

Figures 5C, 5D:
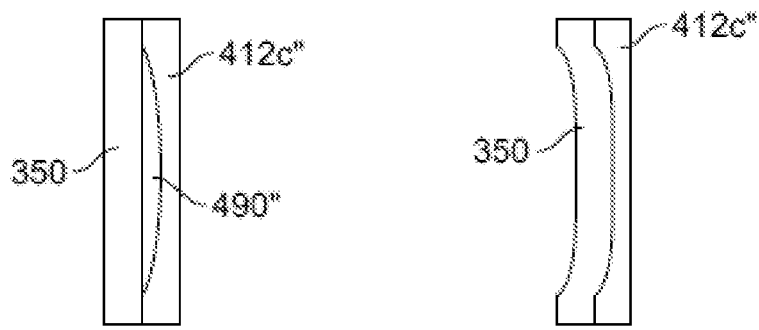
FIG. 5C is a side view of a portion of the outer cuff on an alternate embodiment of a stent in an expanded condition.
FIG. 5D is a side view of a portion of the outer cuff on the stent of FIG. 5C in a collapsed condition.

A similar result to that achieved with the curved struts 412c and 412c' may be obtained without having the struts bow radially inwardly. For example, rather than shape-setting the struts to have a particular curvature to create open spaces between the struts and the outer cuff, the particular struts of interest may be formed with varying widths or thicknesses. For example, FIG. 5C illustrates a strut 412c'' of a stent that is identical to stent 402 in every aspect other than the shape of the struts corresponding to struts 412c and 412d. Struts 412c'' (and the struts corresponding to struts 412d of stent 402) may be formed so that their center portions' have a reduced thickness or diameter compared to their proximal and distal portions. This may be accomplished, for example, by laser cutting or grit blasting struts 412c'' (and the struts corresponding to struts 412d) to have a reduced thickness. In order to create open spaces 490'', the thickness of struts 412c'' should be reduced so that the proximal and distal portions of the struts extend farther radially outward than center portions of the struts. In other words, when the stent incorporating struts 412c'' is in the expanded condition, the sides of the struts 412c'' forming a portion of the lumenal surface of the stent (toward the right in FIG. 5C) should have little or no curvature in the length direction of the struts, whereas the sides of the struts forming a portion of the ablumenal surface of the stent (toward the left in FIG. 5C) should be curved in the length direction of the struts. Thus, whereas all or portions of struts 412c and 412c' have a concavely curved ablumenal surface and a convexly curved lumenal surface in the length direction of the struts, struts 412c'' have a concavely curved ablumenal surface in the length direction of the struts, but a substantially straight lumenal surface in the length direction of the struts.

If a typical strut of stent 402 has a thickness of between about 0.015 and about 0.018 inches, the center portion of struts 412c'' may have a thickness that is reduced by between about 0.004 and about 0.005 inches compared to the other struts (and compared to the proximal and distal ends of struts 412c''. As shown in FIG. 5D, when the stent incorporating struts 412c'' is transitioned to the collapsed condition, outer cuff 350 may at least partially nest or sit within the axially curved surfaces of struts 412c''. It should be understood that although particular shapes, for example of inward curves, are illustrated in FIGS. 4A-5D, any shape of struts 412c and 412d (or struts corresponding to struts 412c and 412d) that provides space between the strut and an adjacent cuff, whether an inner or outer cuff, may be suitable to increase blood flow across that strut and between the cuffs.

Figure 6A:
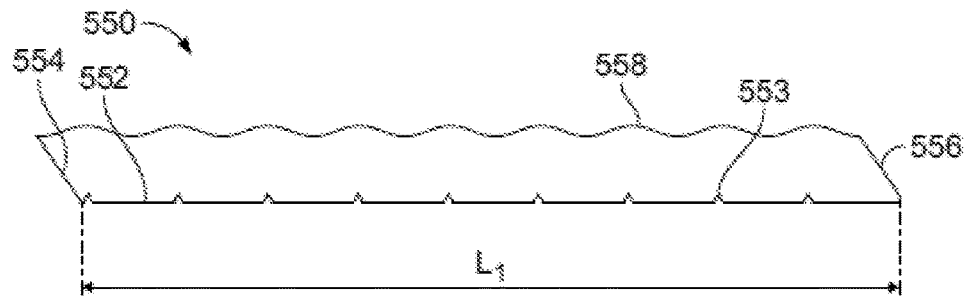
FIG. 6A is a side view of an outer cuff with notches in a flattened condition according to another embodiment of the disclosure.

FIG. 6A illustrates an outer cuff 550 that may be used, instead of outer cuff 350, with an inner cuff 306 and a stent similar or identical to stent 302. Outer cuff 550 generally has a straight inflow or proximal edge 552, correspondingly angled side edges 554 and 556, and a scalloped outflow or distal edge 558, and may be formed from any of the materials noted above for forming the other cuffs described herein, either from a single piece of material, from more than one piece of material, or as a single tubular member (i.e., without side edges 554 and 556). Outer cuff 550 may be wrapped around stent 302 with edges 554 and 556 sutured or otherwise attached to one another. The proximal edge 552 of outer cuff 550 may be attached to the inflow end of stent 302 and/or to inner cuff 306, for example by a continuous line of sutures, so that the outer cuff 550 is positioned at any height between the proximal and distal edges of the inner cuff 306. It should also be understood that although other cuffs herein are shown with a straight distal edge, those cuffs may have a scalloped distal edge as shown in FIG. 6A, or outer cuff 550 may have a substantially straight distal edge. Preferably, the attachment points coupling outer cuff 550 to stent 302 and/or inner cuff 306 are positioned at the peaks of distal edge 558, with the troughs not being directly coupled to the stent or the inner cuff.

Prior to attachment to stent 302 and/or inner cuff 306, the substantially straight proximal edge 552 of outer cuff 550 may be interrupted by a plurality of spaced notches 553. Each notch 553 may be substantially triangular in shape with the base of the triangle (i.e., the base of the notch) positioned along proximal edge 552. The proximal edge 552 of outer cuff 550 has an end-to-end length $L_1$ such that, if outer cuff 550 is wrapped into a tube so that edges 554 and 556 mate, the circumference of the proximal edge will have a greater length than the circumference of the stent 302 at the position at which outer cuff 550 is intended to connect to the stent or inner cuff. Prior to attachment to stent 302, the notches 553 may be closed by coupling the portions of proximal edge 552 adjacent each notch 553 to one another, for example by sutures, adhesives, or any other suitable method, so that the proximal edge 552 is substantially continuous without interruption. Because the portions of proximal edge 552 adjacent each notch 553 are pulled together and coupled to one another, the length $L_2$ of the proximal edge 552 is reduced compared to the length $L_1$. The reduction in the length of the proximal edge 552 upon closing the notches 553 is substantially equal to the aggregate length of the open bases of the notches. The length of the open base of each notch 553 may be selected depending on, for example, the number of cells in the stent 302 and the size of the prosthetic heart valve incorporating the stent and the outer cuff 550. In the case of a 32 mm size valve having nine cells 312 in the proximalmost row, the base of each notch 553 may be between about 0.04 inches and 0.06 inches long, preferably about 0.05 inches long. Preferably, once the open bases of notches 553 are closed, the resulting length $L_2$ of proximal edge 552 is substantially equal to the circumference of the portion of stent 302 or the portion of inner cuff 306 to which the outer cuff 550 will be attached. Because the length of proximal edge 552 decreases upon coupling together the portions of the proximal edge adjacent each notch 553, the material of outer cuff 550 may gather at the positions of the notches 553 to form puckered areas 555, as shown in FIG. 6B.

Figure 6B:
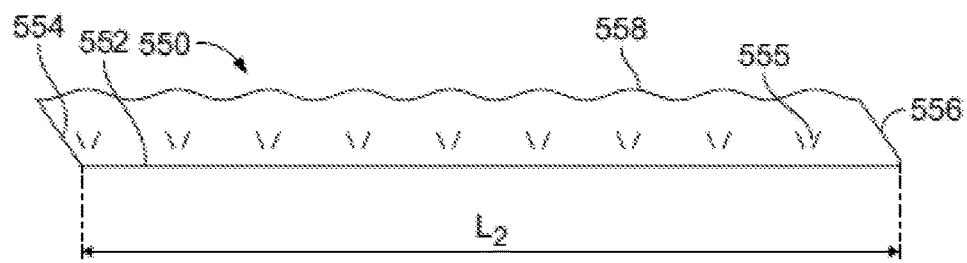
FIG. 6B is a side view of the outer cuff of FIG. 6A after connecting portions of the outer cuff adjacent the notches.
Figure 6C:
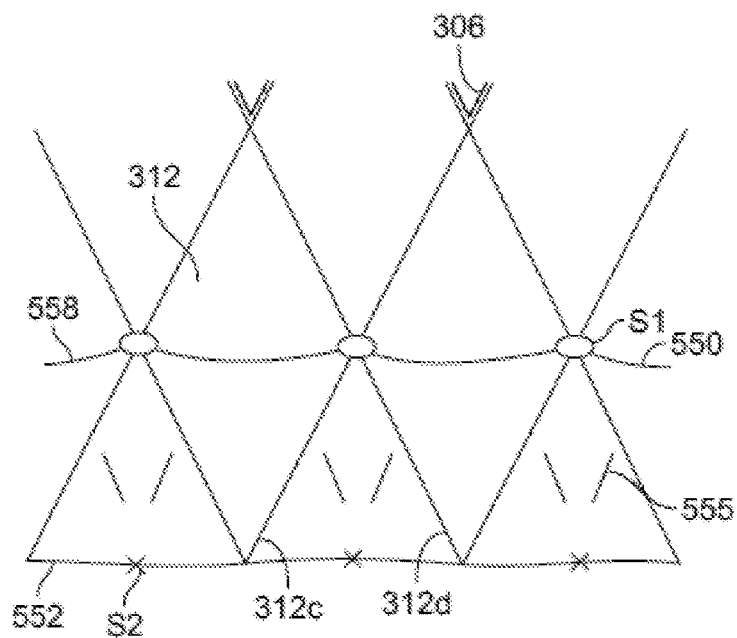
FIG. 6C is a highly schematic view of the outer cuff of FIG. 6A coupled to the stent and/or inner cuff of FIG. 3A.

As shown in FIG. 6C, the distal edge 558 of outer cuff 550 may be attached to stent 302 and/or inner cuff 306, for example on the ablumenal surface of the stent along the proximalmost row of cells 312, at attachment points S1, similar to the attachment of outer cuff 350 to stent 302 and/or inner cuff 306 as described in connection with FIGS. 3A-D. In particular, each peak of distal edge 558 may be attached to stent 302 and/or inner cuff 306 at the locations at which two adjacent cells 312 in the proximalmost row of cells intersect one another, with the portions of the distal edge between attachment points S1 remaining detached from both the stent and the inner cuff. As shown in FIG. 6A, the notches 553 are preferably positioned so they are substantially aligned in the axial direction with the peaks of the distal edge 558 of outer cuff 550. With this configuration, once the outer cuff 550 is coupled to stent 302 and/or inner cuff 306, the puckered portions 555 of the outer cuff are positioned between strut 312c of one cell and strut 312d of a circumferentially adjacent cell in the proximalmost row of cells. The puckered portions 555 of outer cuff 550 reduce the tautness of, or increase the slack in, outer cuff 550 at these positions, allowing for blood located between the outer cuff and inner cuff 306 to more easily migrate in those locations. In particular, retrograde blood flowing into the space between outer cuff 550 and inner cuff 306 may more easily migrate across struts 312c and 312d due to the additional space provided by the puckered portions 555 of the outer cuff which, in turn, allows for the outer cuff to billow outwardly into gaps 200 more completely.

As shown in FIG. 6C, the open bases of notches 553 may be closed with a suture at attachment points S2 prior to coupling the outer cuff 550 to the stent 302 and/or inner cuff 306. The sutures at attachment points S2 may be separate from a substantially continuous suture line coupling the proximal edge 552 of outer cuff 550 to the stent 302 and/or inner cuff 306. However, other methods may be used to couple the proximal edge 552 of outer cuff 550 to the stent 302 and/or inner cuff 306. In one example, the open bases of notches 553 are not closed in a step that is separate from attaching the proximal edge 552 of the outer cuff 550 to the stent 302 and/or inner cuff 306. For example, the proximal edge 552 of outer cuff 550 may be attached to the stent 302 and/or inner cuff 306 by a single continuous suture line, without providing separate sutures to close the open bases of the notches 553. In such a configuration, a suture is used to couple the proximal edge 552 of outer cuff 550 to the stent 302 and/or inner cuff 306, and as the suture approaches a notch 553, the user may gather portions of the proximal edge to close the open base of the notch 553 and continue the suturing so that an additional suture element is not needed to hold the notches 553 in the closed condition. It should be understood that once the portions of the proximal edge 552 of outer cuff 550 adjacent each notch 553 are coupled together, it may not be critical to ensure that the entire space of the notch 553 is completely sealed. For example, because the notches 553 are small and the cycling between systole and diastole is fast, small gaps may remain in outer cuff 550 where the notches 553 are positioned without significant leakage of blood through those gaps. Allowing some amount of gap to remain in notches 553 may even be beneficial. For example, leaving such gaps may provide openings for a user to eliminate air bubbles trapped between outer cuff 550 and inner cuff 306 prior to implanting the prosthetic valve into the patient.

In the embodiment of outer cuff 550 shown in FIGS. 6A-C, the outer cuff includes nine peaks and nine troughs, with nine notches 553 axially aligned with corresponding peaks, and stent 302 includes nine cells 312 in the proximalmost row of cells. Although it may be desirable to have this correspondence between peaks, notches 553, and cells 312, such correspondence is not necessary. For example, the outer cuff 550 may include more or fewer notches 553 than shown, and the number of notches does not need to match the number of cells 312 in the row of cells positioned adjacent the outer cuff. If a relatively large total distance is cut out from the proximal edge 552 of outer cuff 550 by notches 553, a relatively large amount of material of the outer cuff will become puckered, creating additional channels for blood to flow across struts 312c and 312d. However, if too much of the fabric of outer cuff 550 is puckered, the resulting prosthetic heart valve may require greater forces to collapse and load into a delivery device and may even require a larger size delivery device. It should be understood that the outer cuff 550 of FIGS. 6A-B may be used with the stent 402 of FIG. 4A, rather than with stent 302. If outer cuff 550 is used with stent 402, the extra material of the outer cuff in the puckered portions 555 may nest with the bowed struts 412c and 412d of stent 402, similar to outer cuff 350 shown in FIG. 4D, to help reduce the forces encountered upon loading the prosthetic heart valve including outer cuff 550 into the delivery device in a collapsed condition.

Still further, although notches 553 are shown as triangular in shape, other shapes may be suitable. For example, rectangular or trapezoidal shapes may be suitable for the notches 553. However, triangular shapes may help produce a substantially continuous proximal edge 552 as the bases of notches 553 are closed, while at the same time minimizing the size of any gaps that may be formed and through which blood may escape from between outer cuff 550 and inner cuff 306. The size of the notches may also be varied to alter the characteristics of the resulting puckered portions 555. For example, a smaller notch would result in a smaller puckered portion compared to a larger notch. A greater number of smaller notches could therefore result in many smaller puckered portions, while a smaller number of larger notches would result in a fewer larger puckered portions.

Figure 6D:
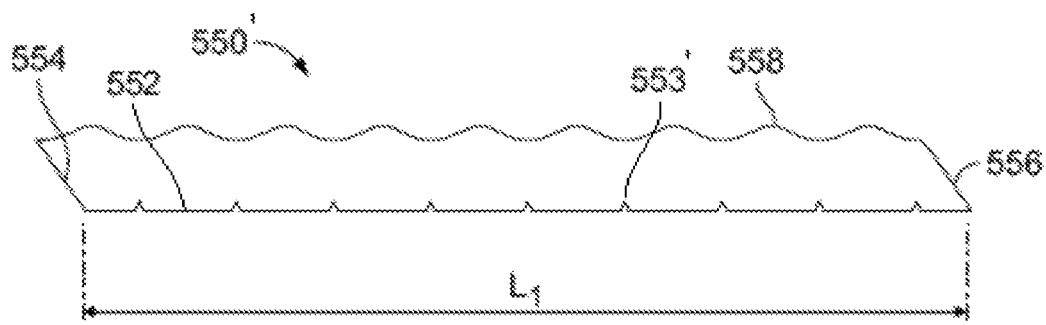
FIG. 6D is a side view of an outer cuff with notches in a flattened condition having an alternate pattern to that shown in FIG. 6A.
Figure 6E:
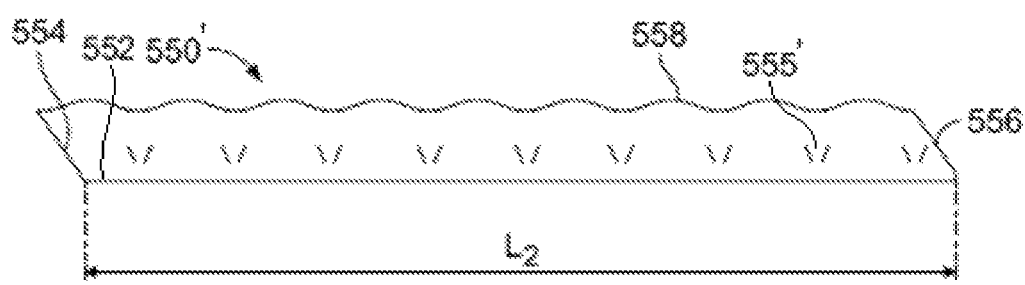
FIG. 6E is a side view of the outer cuff of FIG. 6D after connection portions of the outer cuff adjacent the notches.
Figure 6F:
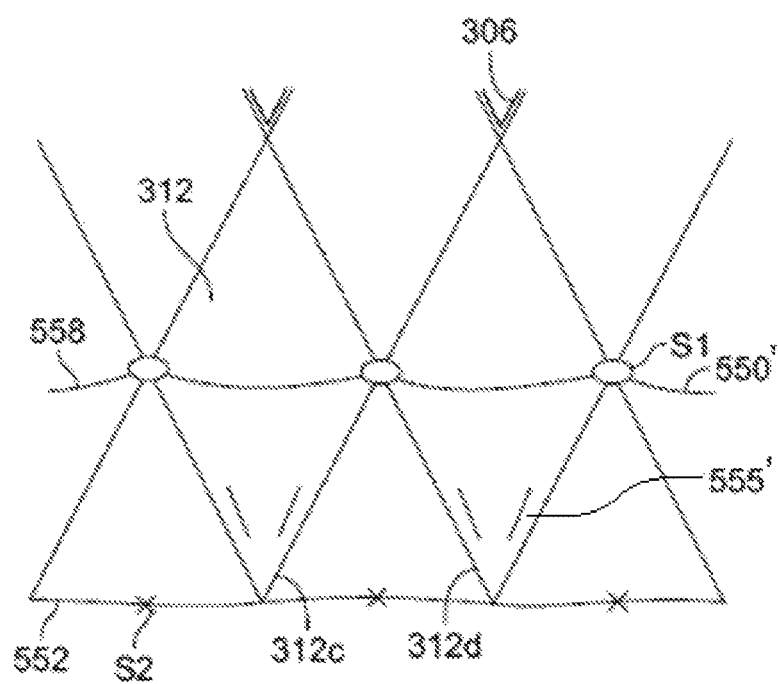
FIG. 6F is a highly schematic view of the outer cuff of FIG. 6D coupled to the stent and/or inner cuff of FIG. 3A.

One example of an alternate configuration of outer cuff 550 is shown as outer cuff 550' in FIGS. 6D-F. Outer cuff 550' is similar or identical to outer cuff 550 in all respects other than the positioning of notches 553', and the resulting position of puckered portions 555'. Whereas notches 553 of outer cuff 550 are illustrated as being in substantial axial alignment with the peaks of distal edge 558, notches 553' of outer cuff 550' may be positioned in axial alignment with the valleys of the distal edge. When the notches 553' are gathered, for example in the same manner as described with respect to notches 553, puckered portions 555' are created, much the same as puckered portions 555. However, because of the alternate positioning of notches 553', puckered portions 555' are created in axial alignment with the valleys of the distal edge 558 of outer cuff 550', as shown in FIG. 6E. As a result, when coupled to a stent and/or inner cuff 306 as shown in FIG. 6F, the puckered portions 555' are positioned between struts 312c, 312d of a cell 312 across which the free distal edge of outer cuff 550' extends. In other words, puckered portions 555' are positioned between adjacent attachment points S1 of the distal edge 558 of cuff 550' to the stent in a circumferential direction of the stent. It should be understood that the variations described with respect to outer cuff 550, for example in terms of the size and number of notches 553, may apply with equal force to outer cuff 550', including in terms of the size and number of notches 553'.

The solutions described above may help create greater billowing of the outer cuff 350 in the presence of retrograde blood flow, and hence greater sealing of the outer cuff against the native valve annulus 250. Still other features may be provided in order to assist the outer cuff 350 from billowing outwardly, for example at a position adjacent to attachment points S1 where the distal edge 358 of the outer cuff is coupled to the stent 302 and/or inner cuff 306.

Figure 7A:
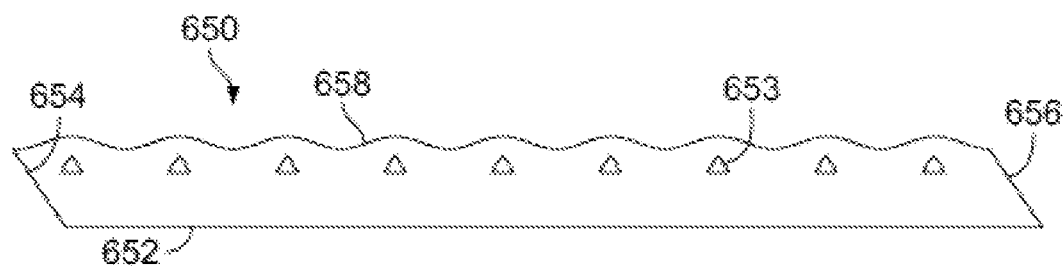
FIG. 7A is a side view of an outer cuff with a plurality openings in a flattened condition.

FIG. 7A illustrates an outer cuff 650 that may capture the retrograde blood flowing past attachment points S1 while enabling that blood flow to enter the space between outer cuff 650 and inner cuff 306 in the restricted space RS between struts 312c and 312d of adjacent cells 312 in the proximalmost row of cells. Outer cuff 650 may be used instead of outer cuff 350 with an inner cuff 306 and a stent similar or identical to stent 302. Outer cuff 650 has a straight inflow or proximal edge 652, correspondingly angled side edges 654 and 656, and a scalloped outflow or distal edge 658, and may be formed from any of the materials noted above for forming the other cuffs described herein, either from a single piece of material, from more than one piece of material, or as a single tubular member. Alternatively, outer cuff 650 may have a substantially straight distal edge 658. Outer cuff 650 may be wrapped around stent 302 with edges 654 and 656 sutured or otherwise attached to one another. The proximal edge 652 of outer cuff 650 may be attached to the inflow end of stent 302 and/or to inner cuff 306, for example by a continuous line of sutures, so that the outer cuff 650 is positioned at any height between the proximal and distal edges of the inner cuff. Preferably, the attachment points S1 coupling outer cuff 650 to stent 302 and/or inner cuff 306 are positioned at the peaks of distal edge 658 (when distal edge 658 is scalloped), with the troughs not being directly coupled to stent 302.

Figure 7B:
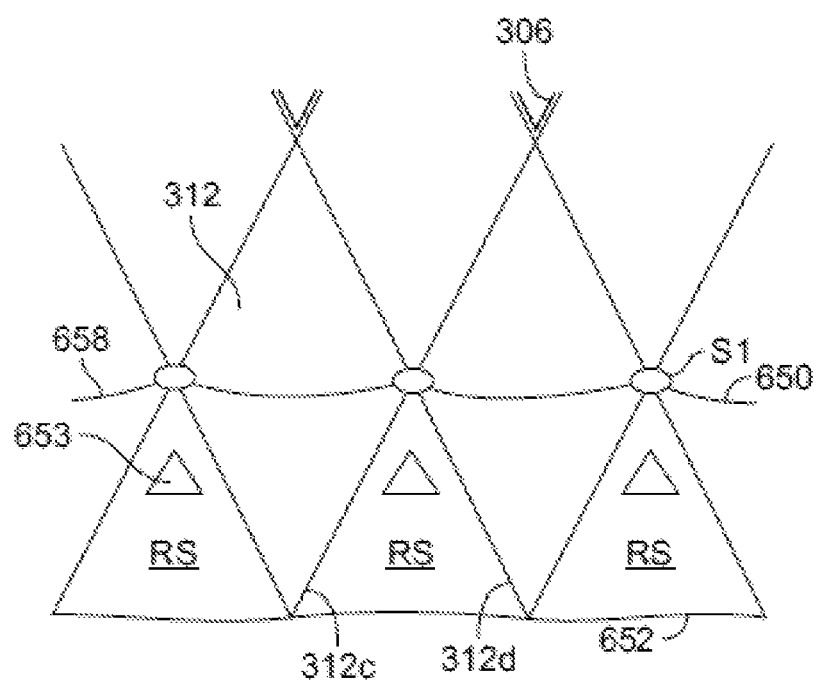
FIG. 7B is a highly schematic view of the outer cuff of FIG. 7A coupled to the stent and/or inner cuff of FIG. 3A.

Outer cuff 650 may additionally include a plurality of apertures 653. In the illustrated example, one aperture 653 is provided for each peak in the distal edge 658 of outer cuff 650. Each aperture 653 may have a substantially triangular shape with a base of the triangle oriented substantially parallel to the proximal edge 652 of outer cuff 650, and a vertex of the triangle positioned closer to the distal edge 658 of the outer cuff. The outer cuff 650 may be formed without the apertures 653, which later may be cut, stamped, or otherwise created in the outer cuff. If each peak in the distal edge 658 is coupled to the stent 302 and/or inner cuff 306 at a point S1, as shown in FIG. 7B, and each aperture 653 is positioned just proximal of each peak, each aperture will also be positioned just proximal of an attachment point S1. With this configuration, retrograde blood flow flowing past an attachment point S1 may be able to enter an aperture 653 and flow into the space between outer cuff 650 and inner cuff 306 in the restricted space RS between the strut 312c of one cell and the strut 312d of an adjacent cell. As a result, retrograde blood flow entering between the inner cuff 306 and the outer cuff 650 in the region between two adjacent attachment points S1 may cause the portion of the outer cuff between the struts 312c and 312d of a single cell 312 to billow away from the inner cuff and the stent 302. On the other hand, retrograde blood flowing past an attachment point S1 and entering restricted space RS through apertures 653 may cause the portion of outer cuff 650 between the strut 312c of one cell 312 and the strut 312d of an adjacent cell to billow away from the inner cuff 306 and the stent 302. Accordingly, the structure of outer cuff 650 enables retrograde blood flowing past attachment points S1 to be captured and the outer cuff to billow outwardly around the entire circumference of stent 302 to improve sealing upon the implantation of the prosthetic heart valve in the native valve annulus.

It should be understood that although apertures 653 are shown as being substantially triangular, other shapes may be suitable. For example, a rectangular shape, a circular shape, a semi-circular shape, a crescent shape, a trapezoidal shape, or one or more slits in the outer cuff material in the circumferential direction may allow blood to enter the space between the outer and inner cuffs. The size of apertures 653 is preferably large enough so that retrograde blood flow may enter the space between outer cuff 650 and inner cuff 306, but not so large so that blood between outer cuff 650 and inner cuff 306 may readily escape through the apertures. In one example in which apertures 653 are triangular, the apex of the triangle closest to the distal edge 658 may be spaced apart from the distal edge 658 between about 0.05 inches and about 0.15 inches, preferably between about 0.07 and about 0.1 inches. In some examples in which apertures 653 are triangular, the base of the triangle may be between about 0.1 inches and about 0.2 inches long, preferably about 0.15 inches long. However, it should be understood that these dimensions are exemplary and may vary based on certain factors, such as the size of the prosthetic valve incorporating the outer cuff 650. Additionally, the apertures 653 are preferably positioned in the distal half or distal third of outer cuff 650 in the axial direction so that the apertures are closer to distal edge 658 than to proximal edge 652. This will enable the retrograde blood to flow into and occupy a greater portion of restricted spaces RS. It is preferable that some axial distance be maintained between the distal edge 658 at attachment points S1 and the apertures 653. If there is only a small amount of material axially separating an aperture 653 from an attachment point S1, there may be a risk that outer cuff 650 may tear between the aperture and the corresponding attachment point. The triangular shapes illustrated may help maximize the strength of the remaining material between an aperture 653 and the distal edge 658 of the outer cuff 650, while also maximizing the size of the aperture, particularly along the proximal base of the triangular shape, through which retrograde blood flow may pass. Although the apertures 653 are illustrated with a triangular shape, it should be understood that one, two, or three of the vertices of the triangle shape may be rounded to eliminate a sharp angle at the corresponding vertex. For example, one or more vertices of each aperture 653 may be triangular with a rounded vertex having a radius of curvature of between about 0.01 inches and about 0.03 inches, preferably about 0.02 inches. Such a rounded vertex may reduce stress concentrations compared to a vertex having a sharp angle, which may in particular reduce the likelihood of the outer cuff 650 adjacent a vertex of a triangular aperture 653 tearing, including in particular the vertex positioned closest to the distal edge 658 of outer cuff 650. It should further be noted that the apertures 653 in outer cuff 650 may be combined with the notches 553 in outer cuff 550, and that outer cuff 650 may also be used with stent 402 instead of stent 302.

It should be understood that although the embodiments of FIGS. 4A-D and 5A-B each show struts being bowed inwardly to create space between an outer cuff and the curved portions of the struts, similar results may be achieved be providing the opposite curvatures in the struts, to create space between an inner cuff and the curved portions of the struts. Similarly, although the embodiment of FIGS. 5C-D illustrate reducing the thickness of struts on an abluminal surface of the struts to create space between the outer cuff and the reduced thickness portions of the struts, alternatively the thickness of the struts may be reduced on a lumenal surface of the struts to create space between the inner cuff and the reduced thickness portions of the struts. Forming the struts with the curvature and/or reduced thickness shown in FIGS. 4A-D and 5A-D may be preferable to such alternative embodiments, however, as the embodiments of FIGS. 4A-D and 5A-D may provide for better anchoring and increased loading forces.

According to a first aspect of the disclosure, a prosthetic heart valve for replacing a native valve comprises:
- a stent extending in an axial direction between an inflow end and an outflow end and having circumferential rows of cells formed by cell struts, the stent having a collapsed condition and an expanded condition;
- a valve assembly disposed within the stent;
- a first cuff disposed on a lumenal surface of the stent; and
- a second cuff having a proximal edge facing toward the inflow end of the stent and a distal edge facing toward the outflow end of the stent, the second cuff being annularly disposed about one of the circumferential rows of cells and positioned radially outward of the first cuff and the stent;
- wherein an ablumenal surface of selected cell struts forming the one circumferential row of cells has a concave curvature in a length direction of the selected cell struts when the stent is in the expanded condition; and/or
- each of the selected cell struts has end portions and a center portion between the end portions, with the stent in the expanded condition a radial distance between the ablumenal surface of the center portion and the second cuff being greater than a radial distance between the ablumenal surface of each end portion and the second cuff; and/or
- a lumenal surface of the selected cell struts has a convex curvature in the length direction of the selected cell struts when the stent is in the expanded condition; and/or
- each of the selected cell struts has a substantially constant strut thickness in a radial direction of the stent; and/or
- a lumenal surface of the selected cell struts is substantially straight in the length direction of the selected cell struts when the stent is in the expanded condition; and/or
- each of the selected cell struts has end portions and a center portion between the end portions, the end portions and the center portion each having a strut thickness in a radial direction of the stent, the strut thickness of the center portion being less than the strut thicknesses of the end portions; and/or
- the concave curvature extends along an entire length of the selected cell struts; and/or
- the concave curvature extends along less than an entire length of the selected cell struts.

According to another aspect of the disclosure, a prosthetic heart valve for replacing a native valve comprises:
- a stent extending in an axial direction between an inflow end and an outflow end, the stent having a collapsed condition and an expanded condition;
- a valve assembly disposed within the stent;
- a first cuff disposed on a lumenal surface of the stent; and
- a second cuff having a proximal edge facing toward the inflow end of the stent and a distal edge facing toward the outflow end of the stent, the second cuff being annularly disposed about the stent and positioned radially outward of the first cuff and the stent, the second cuff including a plurality of notches at spaced apart locations along the proximal edge, each of the notches defining a void in the proximal edge of the second cuff, the second cuff having an initial configuration in which the voids render the proximal edge of the second cuff discontinuous, and a gathered configuration in which the voids are closed so that the proximal edge of the second cuff is substantially continuous, the proximal edge of the second cuff in the gathered configuration having a length that is less than the length of the proximal edge of the second cuff in the initial configuration, the second cuff being coupled to at least one of the stent and the first cuff so that in the expanded condition of the stent, the second cuff is in the gathered configuration; and/or
- with the proximal edge of the second cuff in the gathered configuration and the stent in the expanded condition, the second cuff includes a plurality of puckered portions, each of the puckered portions being aligned in the axial direction with one of the notches and extending farther radially outwardly from the stent than portions of the second cuff positioned circumferentially between adjacent ones of the notches; and/or
- a plurality of attachment points at which the second cuff is coupled to at least one of the stent and the first cuff, each of the puckered portions being positioned between a pair of adjacent attachment points in a circumferential direction of the stent; and/or
- the stent includes a plurality of circumferential rows of cells, the second cuff being in radial alignment with a proximalmost one of the circumferential rows of cells; and/or
- each of the puckered portions is positioned circumferentially between a pair of adjacent cells in the proximalmost row of cells; and/or
- each of the notches has a triangular shape in the initial configuration of the second cuff; and/or
- portions of the proximal edge of the second cuff adjacent each of the notches are coupled to one another in the gathered configuration of the second cuff.

According to yet another aspect of the disclosure, a prosthetic heart valve for replacing a native valve comprises
- a stent extending in an axial direction from an inflow end to an outflow end, the stent having a collapsed condition and an expanded condition;
- a valve assembly disposed within the stent;
- a first cuff annularly disposed on a lumenal or ablumenal surface of the stent; and
- a second cuff having a proximal edge facing toward the inflow end of the stent and a distal edge facing toward the outflow end of the stent, the second cuff being annularly disposed about the stent and positioned radially outward of the first cuff and the stent, the second cuff including a plurality of apertures; and/or
- a plurality of attachment points at which the second cuff is attached to at least one of the stent and the first cuff, each aperture in the second cuff being aligned in the axial direction with a respective one of the plurality of attachment points; and/or
- each of the apertures has a triangular shape; and/or
- the triangular shape of each of the apertures includes a base oriented substantially parallel to the proximal edge of the second cuff and a vertex positioned closer to the distal edge of the second cuff than to the proximal edge of the second cuff; and/or
- the stent includes a plurality of circumferential rows of cells, the second cuff being in radial alignment with a proximalmost one of the circumferential rows of cells, and each of the apertures in the second cuff is positioned circumferentially between a pair of adjacent cells in the proximalmost row of cells.

Although the invention herein has been described with reference to particular embodiments, it is to be understood that these embodiments are merely illustrative of the principles and applications of the present invention. For example, any dimensions provided herein should be understood to be exemplary in nature. It is therefore to be understood that numerous modifications may be made to the illustrative embodiments and that other arrangements may be devised without departing from the spirit and scope of the present invention as defined by the appended claims. For example, features of one embodiment described above may be combined with features of other embodiments described above.

The invention claimed is:

1. A prosthetic heart valve for replacing a native valve, comprising:
   - a stent extending in an axial direction between an inflow end and an outflow end and having circumferential rows of cells formed by cell struts, the stent having a collapsed condition and an expanded condition;
   - a valve assembly disposed within the stent;
   - a first cuff disposed on a lumenal surface of the stent; and
   - a second cuff having a proximal edge facing toward the inflow end of the stent and a distal edge facing toward the outflow end of the stent, the second cuff being annularly disposed about one of the circumferential rows of cells and positioned radially outward of the first cuff and the stent;
   - wherein an ablumenal surface of selected cell struts forming the one circumferential row of cells has a concave curvature in a length direction of the selected cell struts when the stent is in the expanded condition, and
   - wherein each of the selected cell struts has end portions and a center portion between the end portions, and when the stent is in the expanded condition, a radial distance between the ablumenal surface of the center portion and the second cuff is greater than a radial distance between the ablumenal surface of each end portion and the second cuff,
   - wherein a lumenal surface of the selected cell struts is straight in the length direction of the selected cell struts when the stent is in the expanded condition.

2. The prosthetic heart valve of claim 1, wherein the end portions and the center portion of the selected struts each have a strut thickness in a radial direction of the stent, the strut thickness of the center portion being less than the strut thicknesses of the end portions.

3. The prosthetic heart valve of claim 1, wherein the concave curvature extends along an entire length of the selected cell struts.

4. The prosthetic heart valve of claim 1, wherein the concave curvature extends along less than an entire length of the selected cell struts.

* * * * *